United States Patent
Bambawale (10) Patent No.: US 12,114,662 B2
(45) Date of Patent: Oct. 15, 2024

(54) PROCESS, MICROBIAL CONSORTIA AND FORMULATIONS FOR PREVENTING AND ALLEVIATING CITRUS GREENING

(71) Applicant: Omprakash Bambawale, Nagpur (IN)

(72) Inventor: Omprakash Bambawale, Nagpur (IN)

( * ) Notice: Subject to any disclaimer, the term of this patent is extended or adjusted under 35 U.S.C. 154(b) by 619 days.

(21) Appl. No.: 16/640,600

(22) PCT Filed: Jan. 15, 2020

(86) PCT No.: PCT/IB2020/050285
§ 371 (c)(1),
(2) Date: Feb. 20, 2020

(87) PCT Pub. No.: WO2021/105775
PCT Pub. Date: Jun. 3, 2021

(65) Prior Publication Data
US 2021/0360931 A1  Nov. 25, 2021

(30) Foreign Application Priority Data
Nov. 30, 2019 (IN) .............................. 201921049316

(51) Int. Cl.
| | |
|---|---|
| *A01N 63/27* | (2020.01) |
| *A01N 63/38* | (2020.01) |
| *C12N 1/14* | (2006.01) |
| *C12N 1/20* | (2006.01) |
| *C12R 1/38* | (2006.01) |
| *C12R 1/385* | (2006.01) |
| *C12R 1/885* | (2006.01) |

(52) U.S. Cl.
CPC ............ *A01N 63/27* (2020.01); *A01N 63/38* (2020.01); *C12N 1/145* (2021.05); *C12N 1/205* (2021.05); *C12R 2001/38* (2021.05); *C12R 2001/385* (2021.05); *C12R 2001/885* (2021.05)

(58) Field of Classification Search
CPC ........ C12N 1/205; C12N 1/145; A01N 63/27; A01N 63/38; C12R 2001/385; C12R 2001/38; C12R 2001/885
USPC ........................................................ 424/93.3
See application file for complete search history.

(56) References Cited

U.S. PATENT DOCUMENTS

| | | | |
|---|---|---|---|
| 2010/0028303 A1* | 2/2010 | Martin, Jr. .............. | A01N 63/38 424/93.5 |
| 2018/0146683 A1* | 5/2018 | Lorito ..................... | A01N 43/36 |
| 2021/0145010 A1* | 5/2021 | Hänsel .................. | A61K 35/741 |

FOREIGN PATENT DOCUMENTS

WO  WO-2019201777 A1 * 10/2019 ............. A01N 25/02

OTHER PUBLICATIONS

Merriam-Webster, Standardize, Accessed Sep. 20, 2023, Available online at: https://www.merriam-webster.com/dictionary/standardize.*

\* cited by examiner

*Primary Examiner* — Jennifer M. H. Tichy

(57) ABSTRACT

The present disclosure provides a process for preventing, and alleviating citrus greening infection of citrus plants including identifying the causative agent, providing consortia comprising *Trichoderma* spp. and *Pseudomonas* spp. in definite ratios effective in targeting the causative agent *Phytophthora* spp. and thereby preventing or alleviating the citrus greening disease in an effective manner. The present disclosure also provides consortia comprising standardized cultures of *Trichoderma* spp. in varying ratios and *Pseudomonas* spp. in varying ratios effective in preventing and controlling the causative agent *Phytophthora* spp. at different ages of citrus plants and stages of infection. The present disclosure further provides formulations comprising the antagonist microbial consortia and tailor made kits comprising one or more formulations of the present disclosure for managing citrus greening disease.

4 Claims, 4 Drawing Sheets

PROCESS, MICROBIAL CONSORTIA AND FORMULATIONS FOR PREVENTING AND ALLEVIATING CITRUS GREENING

CROSS REFERENCE TO RELATED APPLICATIONS

This application is a national stage entry under 35 U.S.C. Section 371 of International Application No. PCT/IB2020/050285, filed on Jan. 15, 2020, which claims priority to, and the benefit of, Indian Application No. 201921049316, filed on Nov. 30, 2019. The entire disclosures of each of the above applications are incorporated herein by reference.

FIELD OF INVENTION

The present disclosure relates to alleviating citrus greening infection. In particular, the present disclosure provides a process for preventing, and alleviating citrus greening including identification of causative agent and providing effective antagonist microbial consortia and formulations comprising the same in definite ratios.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Citrus greening is an age-old malady of Gondwana origin which has spread to most of the countries wherever citrus was introduced for cultivation with a few exceptions. Citrus greening also referred as Huanglongbing (HLB) received major research thrust when it started inflicting heavy tolls to citrus groves in Brazil and USA since the year 2004-2005. "The universal association of Candidatus Liberibacter asiaticus (CLas) and Asian Citrus Psyllid (ACP, Diphorina citri) with HLB erased virtually all doubt about whether CLas should be a prime subject of research aimed at mitigating HLB" was one of the major recommendations of the Committee on 'Strategic Planning for Florida Citrus Industry: Addressing Citrus Greening Disease' (National Research Council, 2010). This gave impetus to the researchers to focus all the subsequent efforts towards the bacterium (CL species) as the sole cause of the disease.

As the citrus greening that is HLB epidemic raged in 2008, Florida citrus growers created Citrus Research and Development Foundation (CRDF), an oversight responsibility for HLB R&D efforts in Florida. By 2010 CRDF was managing 124 projects on HLBworth $14.3 million. Between 2010 and 2017, CRDF invested $124 million on 398 citrus projects with about 90% focused on citrus greening. USDA (United States Department of Agriculture) supported HLB research with $380 million funding between years 2009 and 2015. Since 2015 it has allocated $43.6 million through National Institute of Food and Agriculture (NIFA). USDA is also actively involved in HLBresearch with expenditure of $21 million. California citrus growers have invested 33 million dollars through Citrus Research Board (CRB). Thus, more than 600 million dollars have been invested in citrus greening research in USA alone (National Academies of Sciences, Engineering and Medicine, 2018) which reflects on the gravity of the situation.

Citrus greening is reported to be widespread in India and CLas is considered to be the principal cause. However, direct pathological interactions between the bacteria and citrus host have not been conclusively documented. The "disease syndrome" ascribed to this disease is also overlapping. Blotchy mottle of the leaves is the most characteristic symptom, but is not specific to citrus greening. Stubborn disease caused by Spiroplasma citri, severe forms of citrus tristeza virus (CTV), water logging and the use of marcots can produce similar symptoms.

The management efforts have all through been centered around CLas and its vector Diphorina citri. In general, there have been inefficacies of integrated disease management measures due to possibly of incorrect assignment of causality.

Two antibiotics-Oxytetracycline and Streptomycin which together were found effective in eliminating CLas bacterium in the HLB-affected citrus plants (Zhang, M., Powell, C. A., Zhou, L., He, Z., Stover, Ed., and Duan, Y. 2011. Chemical compounds effective against the citrus huanglongbing bacterium 'Candidatus Liberibacter asiaticus' in planta. Phytopathology 101: 1097-1103) got "Crisis Exemption" from EPA for large-scale field use for HLB management. The use of antibiotics gave variable results and overall failed to manage the disease.

Pesticides recommended for the vector control are found ineffective possibly because the psyllid vector would not be transferring the real disease pathogen. Prevention of psyllid vector through raising the trees under protective net (Citrus Under Protective Screen—CUPS) has limitations; it is successful only under hydroponics. Biological control of the psyllid vector through Tamarixia radiata has been largely ineffective as the entomophagy does not give adequate control and possibly the psyllid would not be vectoring the real pathogen.

Transgenic citrus trees developed against HLB, using spinach gene, considering CLas as the cause, has not worked to alleviate citrus greening.

Non-efficacy of any of the above strategies indirectly proves that perhaps CLas is not the cause of citrus greening. The limitations of the existing approaches arise mainly from targeting CLas as the real cause of the disease and that appears the main problem why all procedures that were tried to find a solution failed.

Hence there is an unmet need to correctly identify the causative agent, accordingly provide the means and regimen for preventing and alleviating citrus greening, an economically significant disease of citrus plant.

OBJECTS OF THE INVENTION

It is an object of the present disclosure to identify the causative agent responsible for citrus greening disease and provide microbial consortia for targeting the causative agent.

One of the objects of the present disclosure is to provide a process for targeting the causative agent and alleviating citrus greening disease of citrus plant.

Another object of the present disclosure is to provide microbial consortia and formulations comprising the same for preventing and alleviating citrus greening disease of citrus plant by targeting the causative agent.

It is another object of the present disclosure to provide formulations comprising the microbial consortia and a kit comprising the formulation(s) consortium for alleviating citrus greening disease of citrus plant by targeting the causative agent.

SUMMARY

In an aspect the present disclosure provides a process for identifying the causative agent responsible for citrus greening disease and providing microbial consortia and formulation comprising the same for targeting the causative agent.

In an aspect the present disclosure provides a process for identifying the causative agent responsible for citrus greening disease and targeting the causative agent, the process comprising of:
- a) identifying the causative agent by culturing the isolates obtained from the soil samples of the rhizosphere or a plant part of citrus plant showing citrus greening symptoms, the causative agent being identified as *Phytophthora* spp.; and
- b) providing a consortium comprising standardized cultures of *Trichoderma* spp. and formulation comprising the same; or providing a consortium comprising standardized cultures of *Pseudomonas* spp. and formulation comprising the same; or providing both; wherein the steps comprises:
  - i) providing a consortium comprising standardized cultures of *Trichoderma* spp. comprising *Trichoderma* sp. N15C (*Trichoderma reesei* MCC 0174) in combination with one or more of *Trichoderma* spp. selected from *Trichoderma* sp. NC-13 (*Trichoderma longibrachiatum* MCC 0169), *Trichoderma* sp. B5/5 (*Trichoderma erinaceum* MCC 0168), *Trichoderma* sp. B21/3 (*Trichoderma hamatum* MCC 0170), and *Trichoderma* sp. NC-8 (*Trichoderma longibrachiatum* MCC 0171) in a defined ratio(s) for targeting *Phytophthora* spp., and
  - ii) providing a formulation(s) for soil application comprising a consortium comprising standardized culture of *Trichoderma* sp. N15C in combination with one or more of *Trichoderma* spp. selected from *Trichoderma* sp. NC-13, *Trichoderma* sp. B5/5, *Trichoderma* sp. B21/3, and *Trichoderma* sp. NC-8 in a defined ratio(s) at $1\times10^6$ to $1\times10^9$ CFU in nutrient medium and an adjuvant for targeting *Phytophthora* spp.; or
  - iii) providing a consortium comprising standardized cultures of at least two *Pseudomonas* spp. KGH2/3 and NGH2/1 in a defined ratio for targeting *Phytophthora* spp., and
  - iv) providing a formulation for aerial application comprising the consortium comprising standardized cultures of at least two *Pseudomonas* spp. KGH2/3 (*Pseudomonas chlororaphis* subsp. *aurantiaca* MCC 0172) and NGH2/1 (*Pseudomonas aeruginosa* MCC 0173) in a defined ratio at $1\times10^8$ to $1\times10^{11}$ CFU in nutrient medium, and an adjuvant for targeting *Phytophthora* spp.

In another aspect the present disclosure provides a process for preventing or alleviating citrus greening disease including identifying the causative agent, providing microbial consortia and formulations comprising the same for targeting the causative agent and thereby the disease.

In one aspect the present disclosure provides a process for preventing or alleviating citrus greening disease by targeting the causative agent, the process comprises:
- a) identifying the causative agent by culturing the isolates obtained from the soil samples of the rhizosphere of citrus plants as also infected roots and stems showing citrus greening symptoms, the causative agent being identified as *Phytophthora* spp.;
- b) providing a consortium comprising standardized cultures of *Trichoderma* spp. and formulation comprising the same; or providing a consortium comprising standardized cultures of *Pseudomonas* spp. and formulation comprising the same; or providing both; wherein the steps comprises:
  - i) providing a consortium comprising standardized cultures of *Trichoderma* spp. comprising *Trichoderma* sp. N15C (*Trichoderma reesei* MCC 0174) in combination with one or more of *Trichoderma* spp. selected from *Trichoderma* sp. NC-13 (*Trichoderma longibrachiatum* MCC 0169), *Trichoderma* sp. B5/5 (*Trichoderma erinaceum* MCC 0168), *Trichoderma* sp. B21/3 (*Trichoderma hamatum* MCC 0170), and *Trichoderma* sp. NC-8 (*Trichoderma longibrachiatum* MCC 0171) in a defined ratio(s) for targeting *Phytophthora* spp.
  - ii) providing a formulation(s) for soil application comprising a consortium comprising standardized culture of *Trichoderma* sp. N15C in combination with one or more of *Trichoderma* spp. selected from *Trichoderma* sp. NC-13, *Trichoderma* sp. B5/5, *Trichoderma* sp. B21/3, and *Trichoderma* sp. NC-8 in a defined ratio(s) at $1\times10^6$ to $1\times10^9$ CFU in nutrient medium and an adjuvant for targeting *Phytophthora* spp.; or
  - iii) providing a consortium comprising standardized cultures of at least two *Pseudomonas* spp. KGH2/3 and NGH2/1 in a defined ratio for targeting *Phytophthora* spp., and
  - iv) providing a formulation for aerial application comprising the consortium comprising standardized cultures of at least two *Pseudomonas* spp. KGH2/3 (*Pseudomonas chlororaphis* subsp. *aurantiaca* MCC 0172) and NGH2/1 (*Pseudomonas aeruginosa* MCC 0173) in a defined ratio at $1\times10^8$ to $1\times10^{11}$ CFU in nutrient medium, and an adjuvant for targeting *Phytophthora* spp.; and
- c) applying:
  - i) the formulation comprising the *Trichoderma* spp. consortium at a defined dose to soil at a specified period, or
  - ii) the formulation comprising the *Pseudomonas* spp. consortium at a defined dose to aerial parts of the plant at a specified period, or
  - iii) both (i) and (ii), to target the causative agent *Phytophthora* spp. for preventing or controlling the citrus greening disease of citrus plant.

The representative samples of the standardized cultures of *Trichoderma* spp. and *Pseudomonas* spp. have been deposited at National Centre for Microbial Resource-National Centre for Cell Science and International Depositary Authority (IDA) under the Budapest Treaty located at Sai Trinity, Pashan, Pune-411021 and have been identified and assigned the accession numbers as follows:

| Strain Designation as per the present disclosure | Taxonomic Designation as per the IDA | Accession Number |
| --- | --- | --- |
| *Trichoderma* sp. N15C | *Trichoderma reesei* | MCC 0174 |
| *Trichoderma* sp. B5/5 | *Trichoderma erinaceum* | MCC 0168 |
| *Trichoderma* sp. NC-13 | *Trichoderma longibrachiatum* | MCC 0169 |
| *Trichoderma* sp. B21/3 | *Trichoderma hamatum* | MCC 0170 |
| *Trichoderma* sp. NC-8 | *Trichoderma longibrachiatum* | MCC 0171 |

| Strain Designation as per the present disclosure | Taxonomic Designation as per the IDA | Accession Number |
|---|---|---|
| *Pseudomonas* sp. KGH2/3 | *Pseudomonas chlororaphis* subsp. *aurantiaca* | MCC 0172 |
| *Pseudomonas* sp. NGH2/1 | *Pseudomonas aeruginosa* | MCC 0173 |

In one aspect the present disclosure provides a consortium comprising standardized cultures of at least two *Trichoderma* spp. comprising *Trichoderma* sp. N15C in combination with one or more of *Trichoderma* spp. selected from *Trichoderma* sp. NC-13, *Trichoderma* sp. B5/5, *Trichoderma* sp. B21/3, and *Trichoderma* sp. NC-8; wherein the ratio of *Trichoderma* sp. N15C with the other *Trichoderma* sp. is in a range from about 0.5:1 or 1:0.5, to about 1:10.

In one aspect the present disclosure provides a consortium comprising standardized cultures of at least three *Trichoderma* spp. comprising *Trichoderma* sp. N15C in combination with *Trichoderma* sp. NC-13 or *Trichoderma* sp. NC-8; and *Trichoderma* sp. B5/5 or *Trichoderma* sp. B21/3 in a ratio from about 0.5:1:0.5 to about 1:5:0.5.

In one aspect the present disclosure provides a consortium comprising standardized cultures of at least four *Trichoderma* spp. comprising *Trichoderma* sp. N15C, *Trichoderma* sp. B5/5, *Trichoderma* sp. B21/3, and *Trichoderma* sp. NC-13 or *Trichoderma* sp. NC-8 in a ratio from about 0.5:1:1:0.5 to about 3:1:1:5.

In one aspect the present disclosure provides a consortium comprising standardized cultures of *Trichoderma* sp. N15C, *Trichoderma* sp. B5/5, *Trichoderma* sp. B21/3, *Trichoderma* sp. NC-13 and *Trichoderma* sp. NC-8 in a ratio from about 1:0.5:0.5:0.5:1 to about 3:1:1:5:5.

In an aspect the present disclosure provides a formulation for soil application for targeting *Phytophthora* spp. comprising the consortium comprising standardized cultures of at least two, or three, or four or five *Trichoderma* spp. selected from *Trichoderma* spp. N15C, *Trichoderma* sp. NC-13, *Trichoderma* sp. B5/5, *Trichoderma* sp. B21/3, and *Trichoderma* sp. NC-8 in a defined ratio, at $1\times10^8$ to $1\times10^9$ CFU in nutrient medium; and a silica based adjuvant.

In an aspect the present disclosure provides a consortium comprising standardized cultures of at least two *Pseudomonas* spp. KGH2/3 and NGH2/1 in a ratio of about 1:1 to 5:1 for targeting *Phytophthora* spp.

In an aspect the present disclosure provides a formulation for aerial application for targeting *Phytophthora* spp. comprising standardized cultures of at least two *Pseudomonas* spp. KGH2/3 and NGH2/1 in a defined ratio, at $1\times10^8$ to $1\times10^{11}$ CFU in water and an organosilicon adjuvant.

In yet another aspect the present disclosure provides a kit for targeting *Phytophthora* spp. comprising a formulation for soil application comprising consortium comprising standardized cultures of at least two, or three, or four or five *Trichoderma* spp. selected from *Trichoderma* sp. N15C, *Trichoderma* sp. NC-13, *Trichoderma* sp. B5/5, *Trichoderma* sp. B21/3, and *Trichoderma* sp. NC-8 in a defined ratio, at $1\times10^6$ to $1\times10^9$ CFU in nutrient medium, and a silica based adjuvant; optionally a consortium comprising standardized cultures of at least two *Pseudomonas* spp. KGH2/3 and NGH2/1 in a defined ratio, at $1\times10^8$ to $1\times10^{11}$ CFU in water, and an organosilicon adjuvant; and an insert containing instructions for applying the *Trichoderma* spp. formulation in a defined dose and specified period, and optionally for preparing and applying the *Pseudomonas* spp. formulation in a defined dose and specified period.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

FIG. 1: These are photographs showing: (a): plant with yellow shooting; (b): entire plant turning yellow; (c): a number of old trees in a grove showing citrus greening symptoms; (d): an almost dead tree; (e): citrus fruits typically green at the bottom part showing citrus greening infection; (f): close up of leaves showing mottling; (g) stem scrapping from the dead plant showing internal necrosis, a source of causative pathogen identified to be *Phytophthora* spp. post isolation in accordance with the present disclosure; (h) potted nursery plant showing citrus greening caused by *P. citrophthora*; and (i) in-situ grafted plants of *Citrus sinensis* in a farmer's field nursery showing citrus greening infection symptoms of asymmetric blotchy leaf mottle caused by *P. citrophthora* and *P. nicotianae*.

FIG. 2: These are photographs showing: (a): Profusely growing cultures post inoculation of isolates from soil, affected shoots, affected roots of the citrus greening affected citrus plant invariably yielding *Phytophthora* spp. cultures; (b)(i): Vigorous growing *Phytophthora* spp. culture on the left side, (b)(ii) Complete inhibition of the *Phytophthora* spp. culture post applications of formulations comprising consortium of *Trichoderma* spp. and consortium of *Pseudomonas* spp. strains, in defined ratios, on the right side.

FIG. 3: These are photographs showing: (a): *C. sinensis* two and half years old trees affected by greening before the treatment showing yellow leaves; (b): The same trees after six months post treatment with the formulations comprising consortium of *Trichoderma* spp. and consortium of *Pseudomonas* spp. strains, in defined ratios in accordance with the present disclosure, trees are seen recovered from the symptoms of the disease.

FIG. 4: These are photographs showing: (a): A 3 years old C. *Sinensis* grove affected by greening at the beginning of treatment; a number of trees seen affected; (b): The same row of trees after one year seen recovered from the symptoms of the disease after the treatment with the formulations comprising consortium of *Trichoderma* spp. and consortium of *Pseudomonas* spp. strains, in defined ratios in accordance with the present disclosure.

FIG. 5: Itis a photograph showing: A grove after two years of treatments starting from transplanting onwards with the formulations comprising consortium of *Trichoderma* spp. and consortium of *Pseudomonas* strains, in defined ratios in accordance with the present disclosure.

FIG. 6: Are photographs showing: (a) Rough lemon nursery plants of an adjoining farmer which are affected by citrus greening disease showing yellowing and falling of lower leaves; (b) Establishment of a healthy nursery after treatment with the formulations comprising consortium of *Trichoderma* spp. and consortium of *Pseudomonas* spp. strains, in defined ratios in accordance with the present disclosure; (b)(i) Nursery plants showing healthy leaves without disease and no leaf fall; (b)(ii) The nursery plants showing a healthy stand; and (c) An adjoining grower's nursery of grafted plants without any treatment showing typical yellowing stage of the greening disease.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All processes described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms are used herein. To the extent a term used in a claim is not defined below, it should be given the broadest definition persons in the pertinent art have given that term as reflected in printed publications and issued patents at the time of filing.

In an embodiment the present disclosure provides a process for identifying the causative agent responsible for citrus greening disease and providing microbial consortia and formulation comprising the same for targeting the causative agent.

In one embodiment the present disclosure provides a process for identifying the causative agent responsible for citrus greening disease and targeting the causative agent, the process comprises:
  a) identifying the causative agent by culturing the isolates obtained from the soil samples of the rhizosphere or a plant part of citrus plants showing citrus greening symptoms, the causative agent being identified as *Phytophthora* spp.;
  b) providing a consortium comprising standardized cultures of *Trichoderma* spp. and formulation comprising the same; or providing a consortium comprising standardized cultures of *Pseudomonas* spp. and formulation comprising the same; or providing both; wherein the steps comprises:
    i) providing a consortium comprising standardized cultures of *Trichoderma* spp. comprising *Trichoderma* sp. N15C (*Trichoderma reesei* MCC 0174) in combination with one or more of *Trichoderma* spp. selected from *Trichoderma* sp. NC-13 (*Trichoderma longibrachiatum* MCC 0169), *Trichoderma* sp. B5/5 (*Trichoderma erinaceum* MCC 0168), *Trichoderma* sp. B21/3 (*Trichoderma hamatum* MCC 0170), and *Trichoderma* sp. NC-8 (*Trichoderma longibrachiatum* MCC 0171) in a defined ratio(s) for targeting *Phytophthora* spp., and
    ii) providing a formulation(s) for soil application comprising a consortium comprising standardized culture of *Trichoderma* sp. N15C in combination with one or more of *Trichoderma* spp. selected from *Trichoderma* sp. NC-13, *Trichoderma* sp. B5/5, *Trichoderma* sp. B21/3, and *Trichoderma* sp. NC-8 in a defined ratio(s) at $1 \times 10^6$ to $1 \times 10^9$ CFU in nutrient medium and an adjuvant for targeting *Phytophthora* spp.; or
    iii) providing a consortium comprising standardized cultures of at least two *Pseudomonas* spp. KGH2/3 and NGH2/1 in a defined ratio for targeting *Phytophthora* spp.; and
    iv) providing a formulation for aerial application comprising the consortium comprising standardized cultures of at least two *Pseudomonas* spp. KGH2/3 (*Pseudomonas chlororaphis* subsp. *aurantiaca* MCC 0172) and NGH2/1 (*Pseudomonas aeruginosa* MCC 0173) in a defined ratio at $1\times10^8$ to $1\times10^{11}$ CFU in nutrient medium, and an adjuvant for targeting *Phytophthora* spp.

In another embodiment the present disclosure provides a process for preventing or alleviating citrus greening disease including identifying the causative agent, providing microbial consortia and formulations comprising the same for targeting the causative agent and thereby the disease.

In one embodiment the present disclosure provides a process for preventing or alleviating citrus greening disease by targeting the causative agent, the process comprises:
 a) identifying the causative agent by culturing the isolates obtained from the soil samples of the rhizosphere or a plant part of citrus plants showing citrus greening symptoms, the causative agent being identified as *Phytophthora* spp.;
b) providing a consortium comprising standardized cultures of *Trichoderma* spp. and formulation comprising the same; or providing a consortium comprising standardized cultures of *Pseudomonas* spp. and formulation comprising the same; or providing both; wherein the steps comprises:
   i) providing a consortium comprising standardized cultures of *Trichoderma* spp. comprising *Trichoderma* sp. N15C (*Trichoderma reesei* MCC 0174) in combination with one or more of *Trichoderma* spp. selected from *Trichoderma* sp. NC-13 (*Trichoderma longibrachiatum* MCC 0169), *Trichoderma* sp. B5/5 (*Trichoderma* erinaceum MCC 0168), *Trichoderma* sp. B21/3 (*Trichoderma hamatum* MCC 0170), and *Trichoderma* sp. NC-8 (*Trichoderma longibrachiatum* MCC 0171) in a defined ratio(s) for targeting *Phytophthora* spp.,
   ii) providing a formulation(s) for soil application comprising a consortium comprising standardized culture of *Trichoderma* sp. N15C in combination with one or more of *Trichoderma* spp. selected from *Trichoderma* sp. NC-13, *Trichoderma* sp. B5/5, *Trichoderma* sp. B21/3, and *Trichoderma* sp. NC-8 in a defined ratio(s) at $1\times10^6$ to $1\times10^9$ CFU in nutrient medium and an adjuvant for targeting *Phytophthora* spp.,
   iii) providing a consortium comprising standardized cultures of at least two *Pseudomonas* spp. KGH2/3 and NGH2/1 in a defined ratio for targeting *Phytophthora* spp., and
   iv) providing a formulation for aerial application comprising the consortium comprising standardized cultures of at least two *Pseudomonas* spp. KGH2/3 (*Pseudomonas chlororaphis* subsp. *aurantiaca* MCC 0172) and NGH2/1 (*Pseudomonas aeruginosa* MCC 0173) in a defined ratio at $1\times10^8$ to $1\times10^{11}$ CFU in nutrient medium, and an adjuvant for targeting *Phytophthora* spp.; and
c) applying:
   i) the formulation comprising *Trichoderma* spp. consortium at a defined dose to the soil at a specified period, or
   ii) applying the formulation of *Pseudomonas* spp. consortium at a defined dose to the aerial parts of the plant at a specific period, or
   iii) both (i) and (ii) to target the causative agent *Phytophthora* spp. for preventing or controlling citrus greening disease of citrus plant.

In one embodiment the identification of the causative agent is carried out by culturing the isolates obtained from the soil samples of the rhizosphere or a plant part of citrus plants showing citrus greening symptoms in separate PARP media comprising antibiotics and lacking hymexazol fungicide, and studying the colonies formed for identifying the causative agent; wherein the causative agent is identified to be *Phytophthora* spp. The PARP medium comprises antibiotics pimaricin, ampicillin, rifampicin and fungicide PCNB.

In one embodiment the causative agent is isolated from the soil sample of the rhizosphere of citrus plant showing citrus greening infection.

In one embodiment the causative agent is isolated from the plant part selected from root, stem, or leaf of citrus plant showing citrus greening infection.

The representative samples of the standardized cultures of *Trichoderma* spp. and *Pseudomonas* spp. have been deposited at National Centre for Microbial Resource-National Centre for Cell Science and International Depositary Authority (IDA) under the Budapest Treaty located at Sai Trinity, Pashan, Pune-411021 and have been identified and assigned the accession numbers as follows:

| Strain Designation as per the present disclosure | Taxonomic Designation as per the IDA | Accession Number |
|---|---|---|
| *Trichoderma* sp. N15C | *Trichoderma reesei* | MCC 0174 |
| *Trichoderma* sp. B5/5 | *Trichoderma erinaceum* | MCC 0168 |
| *Trichoderma* sp. NC-13 | *Trichoderma longibrachiatum* | MCC 0169 |
| *Trichoderma* sp. B21/3 | *Trichoderma hamatum* | MCC 0170 |
| *Trichoderma* sp. NC-8 | *Trichoderma longibrachiatum* | MCC 0171 |
| *Pseudomonas* sp. KGH2/3 | *Pseudomonas chlororaphis* subsp. *aurantiaca* | MCC 0172 |
| *Pseudomonas* sp. NGH2/1 | *Pseudomonas aeruginosa* | MCC 0173 |

In one embodiment the present disclosure provides a consortium comprising standardized cultures of different *Trichoderma* spp. strains in a defined ratio(s) for targeting the inter and intra-species variability in the three.

In an embodiment the present disclosure provides consortia comprising two or more *Trichoderma* spp. in defined ratio. The consortium comprising *Trichoderma* spp. is standardized to a $1\times10^6$ to $1\times10^9$ CFUs/g or ml using a haemocytometer. The said culture is used within a fortnight of its production.

In one embodiment the present disclosure provides a consortium comprising standardized cultures of at least two *Trichoderma* spp. comprising *Trichoderma* sp. N15C in combination with one or more of *Trichoderma* spp. selected from *Trichoderma* sp. NC-13, *Trichoderma* sp. B5/5, *Trichoderma* sp. B21/3, and *Trichoderma* sp. NC-8; wherein the ratio of *Trichoderma* sp. N15C with the other *Trichoderma* sp. is in a range of about 0.5:1 or 1:0.5, to about 1:10.

In one embodiment the present disclosure provides a consortium comprising standardized cultures of at least three *Trichoderma* spp. comprising *Trichoderma* sp. N15C in combination with *Trichoderma* sp. NC-13 or *Trichoderma* sp. NC-8; and *Trichoderma* sp. B5/5 or *Trichoderma* sp. B21/3 in a ratio of about 0.5:1:0.5 to about 1:5:0.5.

In one embodiment the present disclosure provides a consortium comprising standardized cultures of at least four *Trichoderma* spp. comprising *Trichoderma* sp. N15C, *Trichoderma* sp. B5/5, *Trichoderma* sp. B21/3, and *Trichoderma* sp. NC-13 or *Trichoderma* sp. NC-8 in a ratio of about 0.5:1:1:0.5 to about 3:1:1:5.

In one embodiment the present disclosure provides a consortium comprising standardized cultures of *Trichoderma* sp. N15C, *Trichoderma* sp. B5/5, *Trichoderma* sp.

B21/3, *Trichoderma* sp. NC-13 and *Trichoderma* sp. NC-8 in a ratio of about 0.5:0.5:0.5:1:1 to about 3:1:1:5:5.

In one embodiment the present disclosure provides a formulation for soil application for targeting *Phytophthora* spp. comprising the consortium comprising standardized cultures of at least two, or three, or four or five *Trichoderma* spp. selected from *Trichoderma* sp. N15C, *Trichoderma* sp. NC-13, *Trichoderma* sp. B5/5, *Trichoderma* sp. B21/3, and *Trichoderma* sp. NC-8 in a defined ratio, at $1\times10^6$ to $1\times10^9$ CFU in nutrient medium; and a silica based adjuvant.

In one embodiment the formulation for soil application for targeting *Phytophthora* spp. comprising the *Trichoderma* spp. consortium is provided in the form of talk based formulation using the adjuvant $(Mg_3SiO_{10}(OH)_2)$.

In one embodiment the present disclosure provides a consortium comprising cultures of *Pseudomonas* spp. standardized to a $1\times10^8$ to $1\times10^{13}$ CFUs/ml in water using serial dilutions on nutrient agar plates. The said culture is used within a fortnight of its production.

In one embodiment the present disclosure provides a consortium comprising standardized cultures of at least two *Pseudomonas* spp. KGH2/3 and NGH2/1 in a ratio of about 1:1 to 5:1 for targeting *Phytophthora* spp.

In one embodiment the present disclosure provides a formulation for aerial application for targeting *Phytophthora* spp. comprising standardized cultures of at least two *Pseudomonas* spp. KGH2/3 and NGH2/1 in a defined ratio at $1\times10^8$ to $1\times10^{11}$ CFU in nutrient medium and an organosilicon adjuvant. The formulation is in liquid form.

In one embodiment the organosilicon adjuvant is polyalkyleneoxide modified heptamethyltrisiloxane. The polyalkyleneoxide modified heptamethyltrisiloxane is used in the concentration of 0.001% to 0.003% by weight.

In one embodiment the formulation for aerial application for targeting *Phytophthora* spp. comprising standardized cultures of at least two *Pseudomonas* spp. KGH2/3 and NGH2/1 in a defined ratio is formulated as liquid formulation using the organosilicon adjuvant for example polyalkyleneoxide modified heptamethyltrisiloxane, wherein the consortium is diluted to 1:4 to 1:6 in water and the polyalkyleneoxide modified heptamethyltrisiloxane is used in the concentration of 0.001% to 0.003% by weight. The formulation comprising *Pseudomonas* spp. in the liquid form is applied to aerial parts for example foliage and stem in the form of a spray.

In yet another embodiment the present disclosure provides a kit for targeting *Phytophthora* spp., the kit comprises one or more formulation(s) for soil application comprising consortium comprising standardized cultures of at least two, or three, or four or five *Trichoderma* spp. selected from *Trichoderma* sp. N15C, *Trichoderma* sp. NC-13, *Trichoderma* sp. B5/5, *Trichoderma* sp. B21/3, and *Trichoderma* sp. NC-8 in a defined ratio, at $1\times10^6$ to $1\times10^9$ CFU in nutrient medium, and a silica based adjuvant; optionally a consortium comprising standardized cultures of at least two *Pseudomonas* spp. KGH2/3 and NGH2/1 in a defined ratio, and an organosilicon adjuvant; and an insert containing instructions for applying the *Trichoderma* spp. formulation in a defined dose and specified period, and optionally for preparing and applying the *Pseudomonas* spp. formulation in a defined dose and specified period.

In one embodiment the present disclosure provides a kit for targeting *Phytophthora* spp., the kit comprises one or more formulations selected from:

a formulation comprising a consortium comprising standardized culture at $1\times10^6$ to $1\times10^9$ CFU in nutrient medium of *Trichoderma* sp. N15C in combination with *Trichoderma* sp. NC-13, *Trichoderma* sp. B5/5, *Trichoderma* sp. B21/3 or *Trichoderma* sp. NC-8, the *Trichoderma* sp. N15C being in ratio with the other *Trichoderma* spp. from about 0.5:1 or 1:0.5 to about 1:10; and the adjuvant $(Mg_3SiO_{10}(OH)_2)$;

a formulation comprising a consortium comprising standardized cultures at $1\times10^6$ to $1\times10^9$ CFU in nutrient medium of *Trichoderma* sp. N15C in combination with *Trichoderma* sp. NC-13 or *Trichoderma* sp. NC-8, and *Trichoderma* sp. B5/5 or *Trichoderma* sp. B21/3, in a ratio of about 0.5:1:0.5 to about 1:5:0.5; and the adjuvant $(Mg_3SiO_{10}(OH)_2)$;

a formulation comprising a consortium comprising a standardized culture at $1\times10^6$ to $1\times10^9$ CFU in nutrient medium of, *Trichoderma* spp. N15C in combination with *Trichoderma* sp. B5/5, *Trichoderma* sp. B21/3, and *Trichoderma* sp. NC-13 or *Trichoderma* sp. NC-8, in a ratio of about 0.5:1:1:0.5 to about 3:1:1:5; and the adjuvant $(Mg_3SiO_{10}(OH)_2)$;

a formulation comprising a consortium comprising a standardized cultures at $1\times10^6$ to $1\times10^9$ CFU in nutrient medium of, *Trichoderma* sp. N15C in combination with *Trichoderma* sp. B5/5, *Trichoderma* sp. B21/3, and *Trichoderma* sp. NC-13 and *Trichoderma* sp. NC-8 in a ratio of about 0.5:0.5:0.5:1:1 to about 3:1:1:5:5; and the adjuvant $(Mg_3SiO_{10}(OH)_2)$; or a formulation comprising a standardized culture of at least two *Pseudomonas* spp. KGH2/3 and NGH2/1 in a defined ratio of about 1:1 to about 5:1, at $1\times10^8$ to $1\times10^{11}$ CFU in nutrient medium and an organosilicon adjuvant; and an insert containing instructions for applying the *Trichoderma* spp. formulation in a defined dose and specified period, and optionally for preparing and applying the *Pseudomonas* spp. formulation in a defined dose and specified period.

In certain embodiments preventing or controlling citrus greening disease comprises applying the formulation comprising the consortium of *Trichoderma* spp. to the soil alone or in combination with the formulation comprising *Pseudomonas* spp. to aerial parts at an effective dose before or after planting of citrus plant and as per the age of citrus plant at specific period.

In certain embodiments preventing or controlling citrus greening disease comprises applying to the soil the formulation in the talk form comprising the consortium of *Trichoderma* spp. in different ratios, and subsequently applying the spray on the foliage the formulation comprising *Pseudomonas* spp. in different ratios, at effective doses at the time of planting and subsequently depending upon age of citrus plant.

For growing healthy nursery, treatment of soil beds and seed priming with the formulation comprising *Trichoderma* spp. consortium is done. During all the subsequent growth and/or grafting stages, applications of the formulations comprising the consortium of *Trichoderma* spp. in different ratios on soil in combination with the formulation comprising *Pseudomonas* spp. in different ratios on foliage and stem can be carried out at a defined dose depending upon age of the plant for preventing or alleviating citrus greening.

The formulation comprising the consortium of *Trichoderma* spp. can be applied in the form of talk based formulation to the soil before planting the new grove of citrus plants. Preferably the composition is applied to virgin soils that is the top soil from high elevations where citrus was never grown and citrus not grown in nearby areas. In case of citrus greening infested field, where previously citrus was grown, a pit is dug and soil removed. The pit is filled with virgin soil mixed with the formulation at the rate of about at least 50 gms, preferably about 50 gins to 500 gins of the formulation to establish effective levels of antagonists in the soil and the disease free saplings are planted on such treated soil.

In one embodiment the formulation comprising consortium with all the five *Trichoderma* spp. including the standardized cultures of *Trichoderma* sp. N15C, *Trichoderma* sp. B5/5, *Trichoderma* sp. B21/3, and *Trichoderma* sp. NC-13 and *Trichoderma* sp. NC-8 in a ratio of about 1:0.5:0.5:0.5:1 to about 3:1:1:5:5 and talk as an adjuvant can be scattered at the time of planting in and around the pit at the rate of about 100 grams to about 300 grams per pit.

In one embodiment fifteen days after planting, foliar spray of the formulation is done comprising consortium of *Pseudomonas* spp. KGH2/3 and NGH2/1 in a ratio of about 2:1 of and organosilicon based adjuvant.

For young plants of about six months old, the formulation comprising the consortium including *Trichoderma* sp. N15C, *Trichoderma* sp. B5/5, *Trichoderma* sp. B21/3, and *Trichoderma* sp. NC-13 in a ratio of about 0.5:1:1:0.5 to about 3:1:1:5 is applied at the dose of about 100 grams to about 300 grams per plant. For application of the formulation, soil around the tree trunk is scrapped along 2-3 feet of radius and about 3-6 inches deep, the formulation is scattered and covered with scrapped soil layer.

For about six months old plants, a foliar spray of the formulation comprising consortium of *Pseudomonas* spp. KGH2/3 and NGH2/1 in a ratio of about 1:1 of and organosilicon based adjuvant is applied while taking care to spray over the stem and trunk portion.

For young trees of about twelve to thirteen months, the formulation comprising three *Trichoderma* spp., *Trichoderma* sp. N15C, *Trichoderma* sp. NC-8; and *Trichoderma* sp. B21/3 in a ratio of about 0.5:1:0.5 to about 1:5:0.5 and the talk as an adjuvant can be applied at the dose of about 150 grams to about 400 grams per tree. For application of the formulation, soil around the tree trunk is scrapped along 2-3 feet of radius and about 3-6 inches deep, the formulation is scattered and covered with scrapped soil layer.

For young trees of about twelve to thirteen months, a foliar spray of the formulation comprising consortium of *Pseudomonas* spp. KGH2/3 and NGH2/1 in a ratio of about 2:1 and organosilicon based adjuvant is applied.

For trees of about one and half years age, the formulation comprising three *Trichoderma* spp., *Trichoderma* sp. N15C, *Trichoderma* sp. NC-13; and *Trichoderma* sp. B5/5 in a ratio of about 0.5:1:0.5 to about 1:5:0.5 and the talk as an adjuvant can be applied at the dose of about 150 grams to about 400 grams per tree. For application of the formulation, soil around the tree trunk is scrapped along 2-3 feet of radius and about 3-6 inches deep, the formulation is scattered and covered with scrapped soil layer.

For trees of about one and half years age, a foliar spray of the formulation comprising consortium of *Pseudomonas* spp. KGH2/3 and NGH2/1 in a ratio of about 1:1 and organosilicon based adjuvant is applied.

For trees of about two years age, the formulation comprising three *Trichoderma* spp., *Trichoderma* sp. N15C, *Trichoderma* sp. NC-8; and *Trichoderma* sp. B21/3 in a ratio of about 0.5:1:0.5 to about 1:5:0.5 and the talk as an adjuvant can be applied at the dose of about 250 grams to about 600 grams per tree. For application of the formulation, soil around the tree trunk is scrapped along 3-5 feet of radius and about 3-6 inches deep, the formulation is scattered and covered with scrapped soil layer.

For trees of about two years age, a foliar spray of the formulation comprising consortium of *Pseudomonas* spp. KGH2/3 and NGH2/1 in a ratio of about 2:1 and organosilicon based adjuvant is applied.

For trees of about two and half years and above, the formulation comprising consortium with all the five *Trichoderma* spp. including the standardized cultures of *Trichoderma* sp. N15C, *Trichoderma* sp. B5/5, *Trichoderma* sp. B21/3, and *Trichoderma* sp. NC-13 and *Trichoderma* sp. NC-8 in a ratio of about 1:0.5:0.5:0.5:1 to about 2:1:1:3:3 and talk as an adjuvant can be scattered after ploughing in of cover crop/green manure crop at the rate of about 50 kg to about 250 kg per acre.

For trees of about two and half years and above, a foliar spray of the formulation comprising consortium of *Pseudomonas* spp. KGH2/3 and NGH2/1 in a ratio of about 1:1 and organosilicon based adjuvant is applied.

To protect the foliage or above ground parts from horizontal spread of the disease from any adjoining unprotected citrus grove after every six months foliar sprays may be applied of the formulation comprising consortium of *Pseudomonas* spp. KGH2/3 and NGH2/1 in a ratio of about 2:1 and organosilicon based adjuvant followed by foliar spray of the formulation comprising consortium of *Pseudomonas* spp. KGH2/3 and NGH2/1 in a ratio of about 1:1 and organosilicon based adjuvant.

In certain embodiments the present disclosure provides preventing or controlling the existing citrus greening disease occurring after one or more years of planting, by applying to the soil the formulation in the talk form comprising the consortium of *Trichoderma* spp. in different ratios, and subsequently applying the spray on the foliage the formulation comprising *Pseudomonas* spp. in different ratios, at effective doses depending upon the age of citrus plant.

For the one year old trees showing citrus greening symptoms, the formulation comprising consortium with all the five *Trichoderma* spp. including the standardized cultures of *Trichoderma* sp. N15C, *Trichoderma* sp. B5/5, *Trichoderma* sp. B21/3, *Trichoderma* sp. NC-13 and *Trichoderma* sp. NC-8 in a ratio of about 1:0.5:0.5:0.5:1 to about 3:1:1:5:5 and talk as an adjuvant can be applied at the dose of about 400 grams to about 600 grams per tree by scrapping the soil around the tree along 3-5 feet of radius and about 3-6 inches deep, the formulation is scattered and covered with scrapped soil layer. Simultaneously or subsequently a foliar spray of the formulation comprising consortium of *Pseudomonas* sp. KGH2/3 and NGH2/1 in a ratio of about 1:1 to about 2:1 and organosilicon based adjuvant can be applied.

For trees of about one and half years age infected with citrus greening, the formulation comprising three *Trichoderma* spp., *Trichoderma* sp. N15C, *Trichoderma* sp. NC-13; and *Trichoderma* sp. B5/5 in a ratio of about 0.5:1:0.5 to about 1:5:0.5 and the talk as an adjuvant an be applied at the dose of about 400 grams to about 600 grams per tree by scrapping soil around the tree trunk along 3-5 feet of radius and about 3-6 inches deep, scattering the formulation and covering with scrapped soil layer. Around the same time or consequently, optionally a foliar spray of the formulation comprising consortium of *Pseudomonas* spp. KGH2/3 and NGH2/1 in a ratio of about 1:1 and organosilicon based adjuvant is applied.

For trees of about two years age infected with citrus greening, the formulation comprising three *Trichoderma* spp., *Trichoderma* sp. N15C, *Trichoderma* sp. NC-8; and *Trichoderma* sp. B21/3 in a ratio of about 0.5:1:0.5 to about 1:5:0.5 and the talk as an adjuvant can be applied at the dose of about 400 grams to about 600 grams per tree by scrapping soil around the tree trunk along 4-5 feet of radius and about 3-6 inches deep, scattering the formulation and covering with scrapped soil layer. Around the same time or consequently, optionally a foliar spray of the formulation comprising consortium of *Pseudomonas* spp. KGH2/3 and NGH2/1 in a ratio of about 2:1 and organosilicon based adjuvant is applied.

For trees of about two and half years age or above, the formulation comprising consortium with all the five *Trichoderma* spp. including the standardized cultures of *Trichoderma* sp. N15C, *Trichoderma* sp. B5/5, *Trichoderma* spp. B21/3, *Trichoderma* sp. NC-13 and *Trichoderma* sp. NC-8 in a ratio of about 1:0.5:0.5:0.5:1 to about 2:1:1:3:3 and talk as an adjuvant can be scattered after ploughing in of cover crop/green manure crop at the rate of about 50 kg to about 250 kg per acre. A foliar spray of the formulation comprising consortium of *Pseudomonas* spp. KGH2/3 and NGH2/1 in a ratio of about 1:1 to about 2:1 and organosilicon based adjuvant can be applied around the same time as application of *Trichoderma* spp. followed by another application periodically around every six months.

The treatment in accordance with the present disclosure is effective at the pre-planting stage that is before planting the seedlings or after planting for the plants preferably before 3 years of age for the plants affected with citrus greening disease for satisfactory or complete alleviation of the citrus green disease.

In accordance with certain embodiments, the consortia of *Phytophthora* spp. antagonist microbial strains *Trichoderma* spp. and *Pseudomonas* spp. are isolated from local geographical area and standardized based on their temperature tolerance studies as also their antagonistic abilities across the inter and intra-species variability existing in the three commonly encountered species of *Phytophthora*, for effective alleviation of the citrus greening infection and establishing infection free citrus groves. The consortia and formulations comprising the same can be effectively used to treat the citrus greening disease of citrus species plants, in particular *Citrus reticulata* commonly called as mandarin used for table purposes, peeled easily and taken as a fresh fruit and *Citrus sinensis*, a sweet orange fruit used for juice purposes. The doses of the formulations for the *Citrus reticulata* can be almost half as compared to those applied in case of *Citrus sinensis*.

The present disclosure satisfies the existing needs, as well as others, and generally overcomes the deficiencies found in the existing art.

Advantages of the Present Invention

The present disclosure provides microbial consortia antagonistic to *Phytophthora* spp., formulation comprising the antagonist consortium, a kit comprising the formulation (s) for preventing, controlling, alleviating, and managing citrus greening infection of citrus plant and lacking any resistance development in the pathogen in an effective manner.

The present disclosure provides a process for preventing, alleviating, and managing citrus greening infection of citrus plant including identifying the causative agent specific to host, providing consortia comprising *Trichoderma* spp. and *Pseudomonas* spp. in varying ratios effective in preventing and alleviating the causative agent *Phytophthora* spp. at different ages of citrus plant and stages of infection.

The present disclosure provides formulations comprising the antagonist microbial consortia and tailor made kits comprising one or more formulations of the present disclosure effective in preventing as well as controlling persisting infection of the citrus greening disease.

The application of the formulations comprising the antagonist microbial consortia of the present disclosure helps in avoiding undue sprays required in case of conventional chemical pesticide agents or other bactericides, thus helping the ecosystem.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although processes and materials similar or equivalent to those described herein can be used in the practice of the disclosed processes and compositions, the exemplary processes, devices and materials are described herein. It is to be understood that this disclosure is not limited to particular processes, and experimental conditions described, as such processes and conditions may vary.

Example 1

A. Survey

A Survey was conducted of the Mandarin (*Citrus reticulata*) and sweet orange (*Citrus sinensis*) groves during 2013-2017 in Nagpur and Amravati districts of Vidarbha, Maharashtra, India. Soil and root samples were collected. Detection of typical citrus greening disease was done by visual symptoms seen on leaves, presence of yellow shoot and dieback. Majority of the trees showed leaves having a pattern of yellow and green areas lacking limits between the colours, giving a 'blotchy mottle' appearance (FIG. 1(*f*)). Thicker veins with corky appearance were more common on sweet orange trees. Many trees showed yellow leaves on many shoots (FIGS. 1(*a*) and (*b*)), some of the entire trees had turned yellow (FIG. 1(*c*)), some of the dead plants were also seen (FIG. 1 (*d*)). Citrus fruits of the affected trees clearly showed greening at the bottom side of fruits a typical sign of citrus greening. The stem scrapping from the dead plant shows internal necrosis (FIG. 1(*g*)), which yielded *Phytophthora* spp. upon isolation.

B. Preliminary Confirmation of *Citrus* Greening

Leaf samples from the survey were subjected to iodine test using tincture of iodine (in 1:10 with water). Positive iodine test was recorded on all the sweet orange trees showing typical citrus greening symptoms.

C. Association of *Phytophthora* Spp. (PPB=Putative Pathogen B) with *Citrus* Greening Symptoms Soil samples collected from the rhizosphere and infected roots and stems of trees showing citrus greening symptoms were subjected to the standard isolation procedure for *Phytophthora* spp. using bait technique (Drenth. A. and Sendall. B. 2001. Practical guide to detection and identification of *Phytophthora*. CRC for Tropical Plant Protection, Indooroopilly QLD 4068, Australia. 41 pages). PARPH medium is generally used by Citrus Research Institutes the world over for *Phytophthora* isolation. Hymexazol is a fungicide which is a component of PARPH medium as it is found to suppress most *Pythium* species (Masago et al. 1977) but it can also inhibit some *Phytophthora* species including *P. cinnamomi, P. citrophthora* and *P. palmivora*. It was seen during repeated isolations that hymexazol constituent of the PARPH medium was detrimental to *Phytophthora* spp. from citrus drastically reducing the colony vigour even to the extent that *Phytophthora* spp. was altogether undetectable giving a false conclusion that *Phytophthora* spp. was not associated with citrus greening symptoms. Therefore, PARPH medium lacking hymexazol was used for isolation of causative agent. In such medium plating of isolations from soil or affected roots and stems from the citrus greening affected citrus groves invariably showed *Phytophthora* spp. profuse growth (FIG. 2

TABLE 1-continued

Ratios of *Trichoderma* spp. and *Pseudomonas* spp. consortia for establishing new nurseries and continued application:

| S. No. | Stage of Application | Microbial spp. | Strains | Ratio |
|---|---|---|---|---|
| 2 | 15 days after planting | *Pseudomonas* | KGH2/3 and NGH2/1 | 02:01 |
| 3 | About 6/3 months after planting/seeding | *Trichoderma* | B5/5, NC-13, B21/3 and N15C | 1:0.5:1:0.5 |
| 4 | About 6/3 months after planting/seeding | *Pseudomonas* | KGH2/3 and NGH2/1 | 01:01 |
| 5 | About 12/10 months old trees/seedlings | *Trichoderma* | B21/3, NC-8 and N15C | 0.5:2:1 |
| 6 | About 12/10 months old trees/seedlings | *Pseudomonas* | KGH2/3 and NGH2/1 | 02:01 |
| 7 | About 18/15 month old trees/grafted seedlings | *Trichoderma* | B5/5, NC-13 and N15C | 0.5:2:1 |
| 8 | About 18/15 month old trees/grafted seedlings | *Pseudomonas* | KGH2/3 and NGH2/1 | 01:01 |
| 9 | Two years old trees | *Trichoderma* | B21/3, NC-8 and N15C | 0.5:2:1 |
| 10 | Two years old trees | *Pseudomonas* | KGH2/3 and NGH2/1 | 02:01 |
| 11 | Two and a half years old trees and beyond | *Trichoderma* | B5/5, NC-13, B21/3, NC-8 and N15C | 05:1:0.5:1:1 |
| 12 | Two and a half years old trees and beyond | *Pseudomonas* | KGH2/3 and NGH2/1 | 01:01 |

TABLE 2

Ratios of *Trichoderma* spp. and *Pseudomonas* spp. consortia for application to already infected plants/trees:

| S. No. | Stage of Application | Microbial spp. | Strains | Ratio |
|---|---|---|---|---|
| 1 | Twelve to thirteen months old trees | *Trichoderma* | B5/5, NC-13, B21/3, NC-8 and N15C | 1:3:1:3:2 |
| 2 | Twelve to thirteen months old trees | *Pseudomonas* | KGH2/3 and NGH2/1 | 02:01 |
| 3 | One and half years old trees | *Trichoderma* | B5/5, NC-13 and N15C | 0.5:2:1 |
| 4 | One and half years old trees | *Pseudomonas* | KGH2/3 and NGH2/1 | 01:01 |
| 5 | Two years old trees | *Trichoderma* | B21/3, NC-8 and N15C | 0.5:2:1 |
| 6 | Two years old trees | *Pseudomonas* | KGH2/3 and NGH2/1 | 02:01 |
| 7 | Two and a half years old trees and beyond | *Trichoderma* | B5/5, NC-13, B21/3, NC-8 and N15C | 05:1:0.5:1:1 |
| 8 | Two and a half years old trees and beyond | *Pseudomonas* | KGH2/3 and NGH2/1 | 01:01 |

Example 3

In-Vitro Testing

Figure 1:
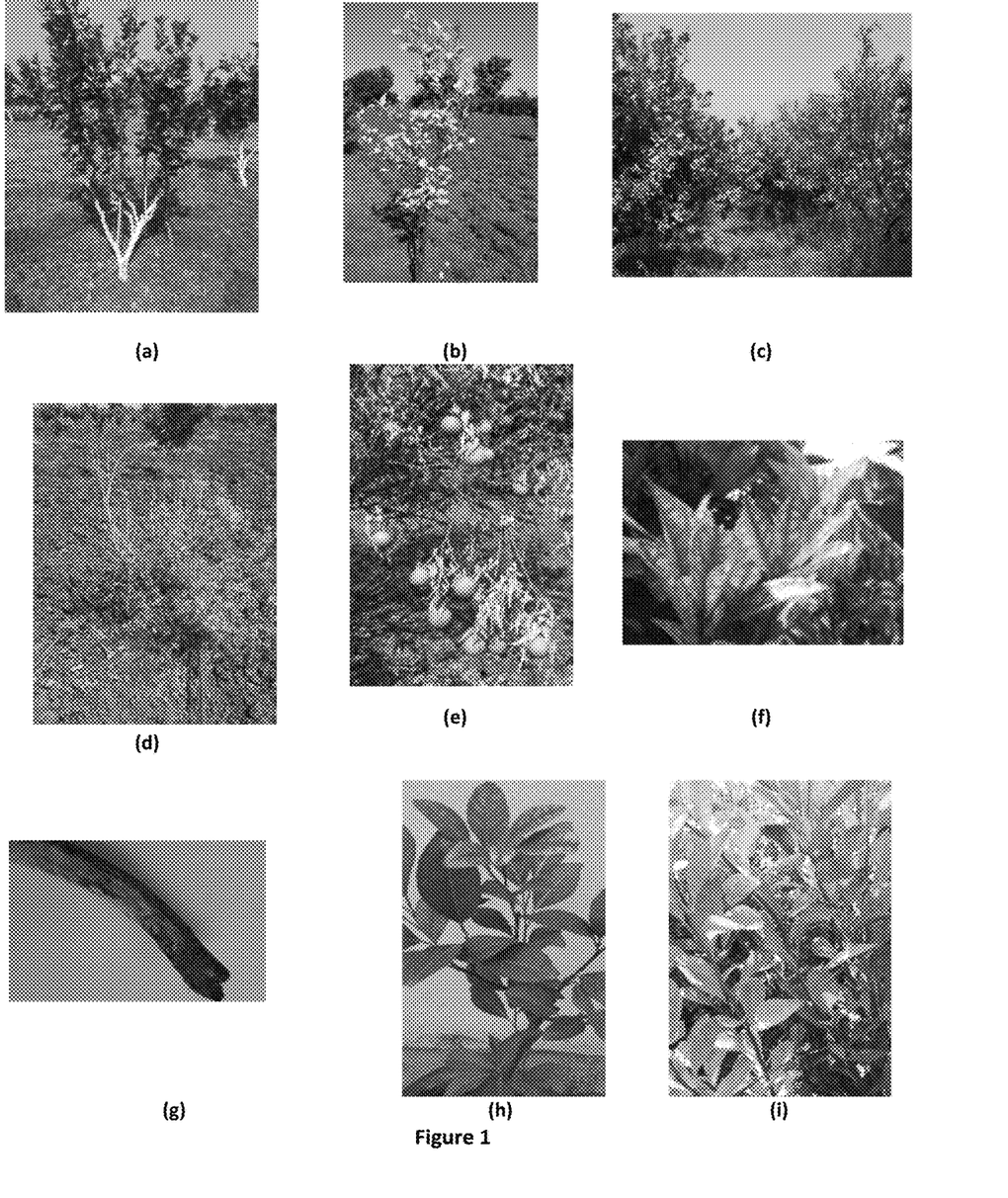
Figure 2:
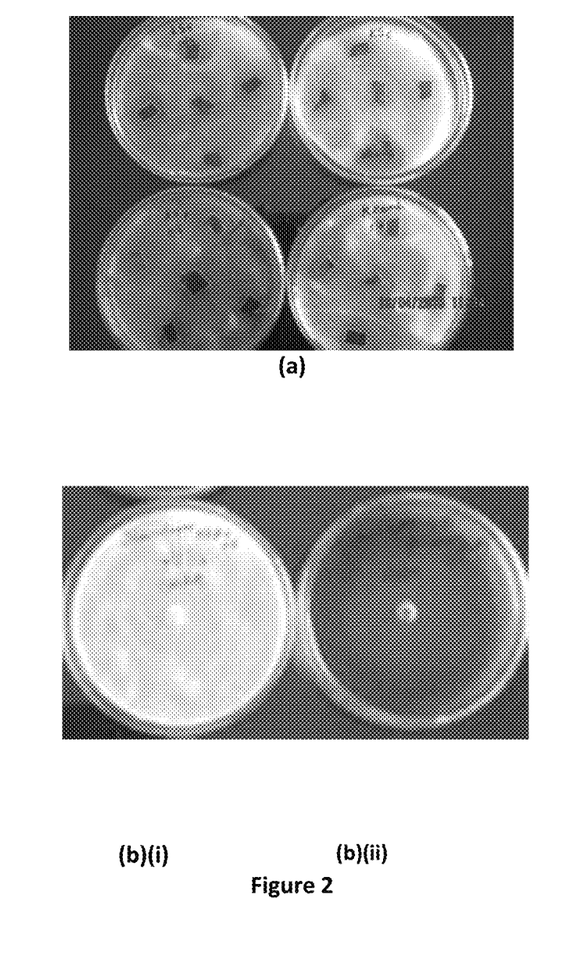

All the strains of *Phytophthora* spp. as well as *Trichoderma* spp. and *Pseudomonas* spp. grew well on a medium comprising 50% strength of V8 agar (HiMedia) plus 50% strength of Potato Dextrose Agar. This medium was therefore used in the evaluation of antagonistic abilities using dual culture technique. At least 30 *Phytophthora* spp. cultures showing variable morphological features in *P. citrophthora*, *P. nicotianae* and *P. palmivora* were challenged with the 7 antagonists. The evaluation process was repeated twice to ensure consistency of results. *Phytophthora* spp. gets totally or >80 percent killed within 4 to 6 days with these antagonists as can be seen from FIG. 2(*b*) right hand side plate showing colony completely killed compared to profuse growth of *Phytophthora* on the left side plate in FIG. 2 (*b*).

Example 4

Field Testing

Field evaluations were carried out at different citrus groves in Katol Tehsil of Nagpur district. Maharashtra from 2016. The citrus trees in grove were of variable ages starting from planting, 1, 1.5, 2, 2.5 years and above as well as new nurseries were developed right from the planting stage.

Trial 1—Mandarin Orange Grove with Tree of Age Two Years and Above:

Out of 47 trees in this small grove 28 trees showed the symptoms of citrus greening with yellow mottled leaves and yellow shoots. The trial was initiated on Aug. 17, 2016 with applications of 100 kg per acre of the talk based formulation comprising *Trichoderma* spp. consortium with all the five species in a ratio as per Table 2. The dry formulation was scattered on the scrapped soil surface of 3 feet radius around tree trunks and covered back with scrapped soil. Followed by soil application, foliar spray of the liquid formulation comprising the *Pseudomonas* spp. consortium in the ratio of 1:1 of strains KGH2/3 and NGH2/1 as per Table 2, along with the silicon based adjuvant (Filwet) was applied. Further treatment regimens were followed as per Table 2. Observations were recorded in December 2018. There were 3 dead trees, one tree still showed yellow branches whereas 24 trees fully recovered. The recovery success was 89% with trees showing healthy green leaves without mottle, yellow shoots or dieback symptoms. In many other small trials, it was seen that affected mandarin trees responded well and quickly to the treatment compared to the sweet orange trees which are highly susceptible to *Phytophthora* spp.

Figure 3:
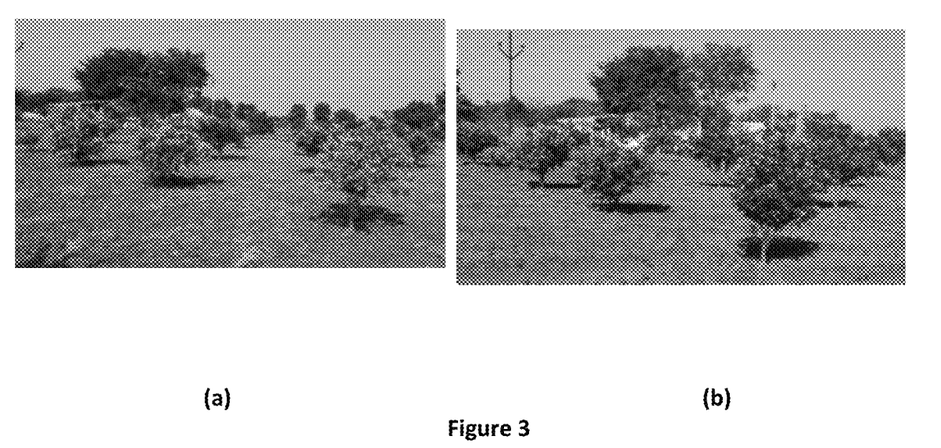

Trial 2—Two and Half Years Old Sweet Orange Grove:

A trial was conducted on a small and neglected grove with lot of weed, poor nutrition and irregular irrigation. The symptoms of citrus greening were clearly visible with yellow shoots and branches (FIG. 3(*a*)). The field was challenging as mandarin orange was grown earlier and the trees of 20+ years when got badly affected by *Phytophthora* spp. were removed and a fresh planting of sweet orange was made. Treatment was initiated on 3 yellow looking trees in January 2016. Six more trees were initiated for treatment on 20 Nov. 2016 and 22 more were started with treatment on 3 Jan. 2017. The talk based formulation comprising consortium of three species of *Trichoderma* spp. in a ratio as per Table 2 was applied to the scrapped soil surface along 4 feet radius from the trunk at the dose of 500 grams/tree and covered back with scrapped soil. Followed by soil application, foliar spray of the liquid formulation comprising the *Phytophthora* spp. consortium in the ratio of 2:1 of strains KGH2/3 and NGH2/1 as per Table 2, along with the silicon based adjuvant (Filwet) was applied. Further treatments of *Trichoderma* spp. and *Pseudomonas* spp. consortia were continued as per Table 2. Observations recorded on 15 Oct. 2017 showed that out of 31 trees treated, 7 trees which were very heavily infected initially were either dead or dying, whereas 24 trees (FIG. 3(*b*)) had recovered completely. The recovery was 77.41%.

Figure 4:
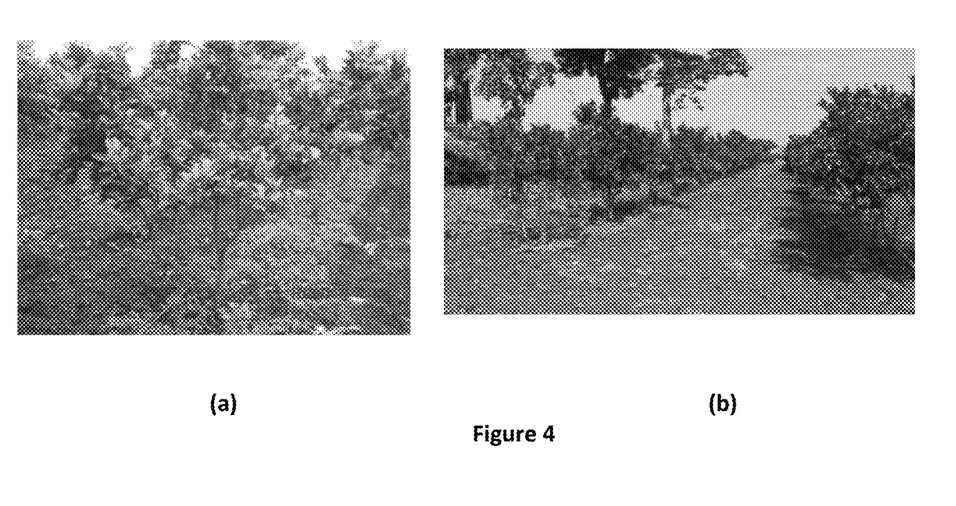

In yet another similar nearby trial on *Citrus sinensis* two plus year old grove where similar regimens of the two consortia of *Trichoderma* spp. and *Pseudomonas* spp. were followed as per Table 2, the results showed that out of 335 citrus greening affected trees that were treated, 75.5 percent trees survived the initial disease (FIG. 4 (*a*)) and improved substantially (FIG. 4 (*b*)).

Trial 3—Virgin Field (Citrus Never Grown in the Field) at the Time of Sweet Orange Planting:

A trial was initiated with *Citrus sinensis* saplings grown in a nursery in Katol Tehsil with planted saplings already having some level of apparent disease infection with *Phytophthora* spp. as verified by citrus greening symptoms and from isolations from the soil samples of the nursery. The below treatment regimen was followed using the talk based formulations comprising consortium of different strains of *Trichoderma* spp. at defined ratios and the liquid formulations comprising consortium of *Pseudomonas* spp. at defined ratios as per Table 1:

A. At the time of planting: On 15 and 16 Jul. 2017 the pits were first treated with 75-100 grams per plant of the talk based formulation comprising *Trichoderma* consortium with all five species at the ratio as per Table 1, B. 15 days after planting: The liquid formulation comprising the consortium of *Pseudomonas* spp. strains KGH2/3 and NGH2/1 in the ratio of 2:1 as per Table 1, along with the organosilicon based adjuvant (Filwet) was applied by foliar spray.

C. Six months after planting: Soil application at the dose of 200 grams/tree of the talk based formulations comprising four strains of *Trichoderma* spps. B5/5, NC-13, B21/3 and N15C in the ratio of 1:0.5:1:0.5 respectively. Soil around the tree trunk was scrapped along 2 feet radius, and 4 inch depth and the formulation was scattered and covered with the scrapped soil layer.

D. Six months after planting: Foliar spray of *Pseudomonas* spp. consortium of strains KGH2/3 and NGH2/1 in the ratio of 1:1 with the adjuvant Filwet was applied. Care was taken to cover stem and trunk portion.

E. Twelve to thirteen months after planting: Soil application of the talk based formulation comprising three strains of *Trichoderma* spp. in the ratio of 0.5:2:1 of B21/3, NC-8 and N15C was applied to the 3 feet radius scrapped soil surface from the trunk at the rate of 300 grams/tree and covered with a soil layer as in C above.

F. Twelve to thirteen months after planting: Foliar spray of *Pseudomonas* spp. consortium of strains KGH2/3 and NGH2/1 in the ratio of 2:1 along with the organosilicon based adjuvant (Filwet) was applied.

G. One and half years old trees: Soil application of the talk based formulation comprising three strains of *Trichoderma* spp. B5/5, NC-13 and N15C in the ratio of 0.5:2:1 was applied to the 3 feet radius scrapped soil surface from the trunk at the rate of 300 grams/tree and covered with a soil layer as in C above.

H. One and half years old trees: Foliar spray of *Pseudomonas* spp. consortium of strains KGH2/3 and NGH2/1 in the ratio of 1:1 along with the organosilicon based adjuvant (Filwet) was applied.

I. Two years old trees: Soil application of the talk based formulation comprising three strains of *Trichoderma* spp. B21/3, NC-8 and N15C in the ratio of 0.5:2:1 was applied to the 4 feet radius scrapped soil surface from the trunk @500 grams/tree and covered with a soil layer as in C above.

J. Two years old trees: Foliar spray of *Pseudomonas* spp. consortium of strains KGH2/3 and NGH2/1 in the ratio of 2:1 along with the organosilicon based adjuvant (Filwet) was applied.

Figure 5:
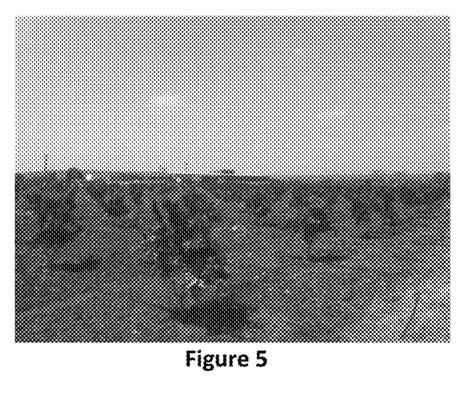
Figure 6:
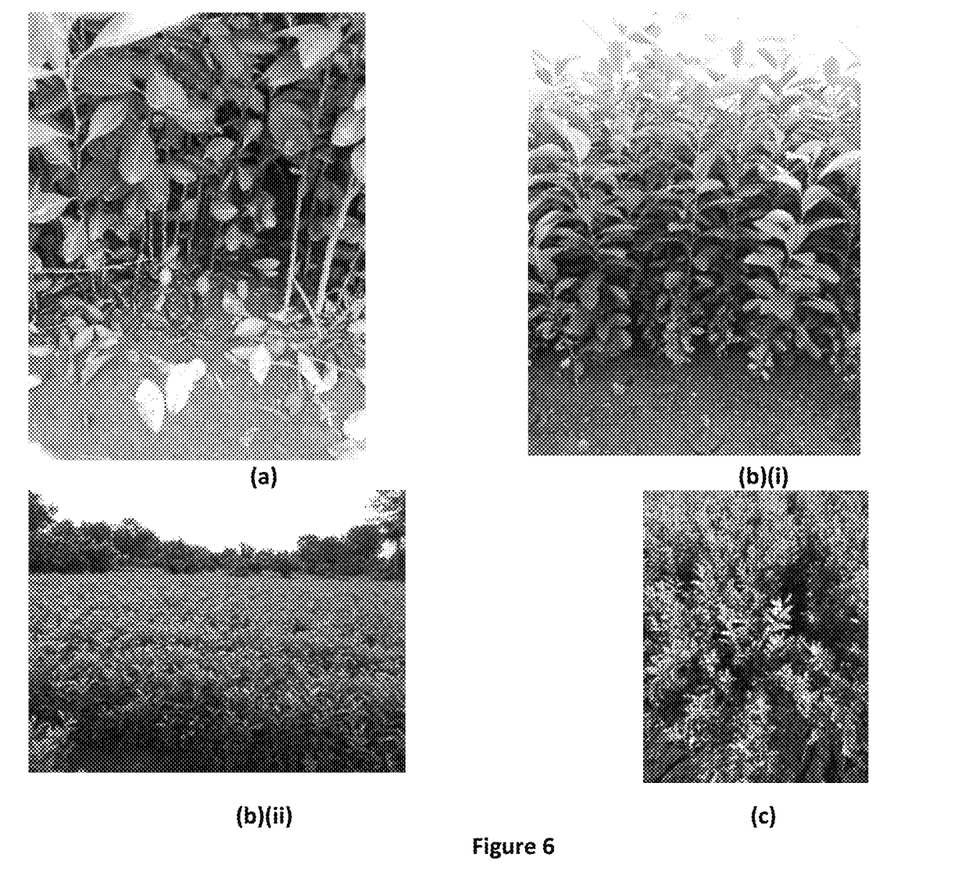

Out of the 240 plants treated only 2 saplings which were heavily infected and almost dead initially were dead, 4 plants showed some yellowing of branches, but 234 were growing vigorously and were healthy (FIG. 5). It was a good stand of 97.5% trees surviving well as noted on 17 Jul. 2019. To compare the difference without treatment, saplings from the same nursery with some infection of *Phytophthora* spp. were planted at another village about 25 km from Nagpur in July 2018. This field was also virgin and citrus was never planted here. It was found that out of 515 plants observed in January 2019, there were 40 plants which were dead and another 46 plants showed typical HLB symptoms. Thus, in just 6 months there was a disease to the extent of 16.69% whereas at the Katol grove treated as mentioned above, even after 2 years the disease was as low as 2.5%.

Trial 4—Development of Disease Free Nursery from the One Affected by *Phytophthora* spp.:

Citrus nurseries in Katol region in Maharashtra, India were closely observed for the symptoms of citrus greening due to *Phytophthora* spp. since August 2016. In this area (Katol) seeds of rough lemon (*Citrus jambheri*) or Rangpur lime (*Citrus limonia*) are sown as the rootstocks in the month of October-November. Open nursery fields are invariably affected by *Phytophthora* spp. with the nearby mother trees exhibiting almost entire citrus greening disease syndrome. In such nurseries, some of the seedlings die early with damping off like symptoms. The healthy-looking seedlings are transplanted in plastic bags or in the open field in July next year. Here the plants develop typical symptoms of *Phytophthora* spp. and rouging is done to remove such plants. The remaining grown up plants are grafted with the buds taken from adjoining infected mother trees in the month of January next year. The grafted plants are then sold in the month of July. Thus, it is a cycle of one year and 7 months when the plants throughout get exposed to *Phytophthora* spp. All through the growth stages of nursery growing, citrus greening like disease can be observed and *Phytophthora* spp. was isolated from such plants showing typical citrus greening symptoms. It is noted in literature that the CLas bacteria is slow growing and symptom appearance on the newly planted trees often takes a few years. It is demonstrated here that it is not so and the trees exhibiting typical citrus greening symptoms can be seen on nursery plants as well as on just one year old plants and can be recognized with naked eye easily. One such open field nursery in Katol Tehsil was adopted to take up trials with the two consortia. The entire course of development spanned around a period of about 20-22 months. The entire treatment regimen was followed as per Table 1 indicating aspects for nursery preparation. The formulation comprising consortia of *Trichoderma* spp. strains B5/5, NC-13, B21/3, NC-8 and N15C in a ratio of 1:3:1:3:2 as perwas scattered on and around the raised beds at the rate of about 100 grams/m$^2$. The priming of *Citrus jambheri* and *Citrus limonia* seed was done with a water-based formulation of NC-13 at a concentration of $1\times10^9$ CFUs/ml overnight. The seeds were then dried under shed and sown on the beds prepared as above.

Sowing was done in the month of October/November. Subsequently, surface soil application of the formulation of the consortium comprising *Trichoderma* spp. strains B5/5, NC-13, B21/3 and N15C in the ratio of 1:0.5:1:0.5 at the rate of 100 grams/m² of the beds was done in January-February. Foliar applications of the formulation comprising consortium of the *Pseudomonas* spp. strains KGH2/3 and NGH2/1 in the ratio of 1:1 was done in January-February with adjuvant Filwet. Subsequently after about 7 months in July the seedlings so prepared were transplanted in a fresh field where soil application of the formulation of the consortium comprising *Trichoderma* strains B21/3, NC-8 and N15C in a ratio of 0.5:2:1 was done at the rate of 100 grams/m² Immediately after transplanting the plants were sprayed with the consortium of *Pseudomonas* spp. KGH2/3 and NGH2/1 in the ratio of 2:1 with adjuvant Filwet. In January next year the seedlings were grafted with buds from the mother plants of either *Citrus sinensis* or *Citrus reticulata*. At this stage consortium of *Trichoderma* spp. strains B5/5, NC-13 and N15C in a ratio of 0.5:2:1 was applied to the beds@100 grams/m². Foliar applications of the formulation comprising consortium of the *Pseudomonas* spp. strains KGH2/3 and NGH2/1 in the ratio of 1:1 was done in January-February with adjuvant Filwet. Plants so developed were ready by July for establishing a new citrus grove.

Such treatment eliminate/substantially reduces the incidence of citrus greening in *Citrus sinensis* and *Citrus reticulata*. The trial was carried out for a period of over 20-22 months and results were observed to be very promising with almost no disease in the nursery as seen from the photographic evidence of treated versus untreated adjoining farmer's nurseries as depicted in FIG. 6: FIG. 6 (*a*): Untreated rough lemon nursery plants of adjoining farmer's field shows yellowing and falling of lower leaves; FIG. 6 (*b*)(i): Treated nursery plants with the two consortia regimes shows healthy lush green leaves without any leaf fall; FIG. 6(*b*)(ii): The two consortia treated nursery with 100/% plant stand; and FIG. 6 (*c*): Adjoining farmer's nursery of grafted plants without any treatment showing typical yellowing stage of the greening disease.

From the foregoing, it will be appreciated that, although specific embodiments of the invention have been described herein merely for purposes of illustration, various modifications may be made without deviating from the spirit and scope of the invention and should not be construed so as to limit the scope of the invention or the appended claims in any way.

I claim:

1. A consortium for preventing or alleviating *Citrus* Greening disease by targeting a causative agent *Phytophthora* spp. selected from *Phytophthora citrophthora, Phytophthora nicotianae* and *Phytophthora palmivora*, the consortium comprising cultures of at least two *Trichoderma* spp., each at $1\times10^6$ to $1\times10^9$ CFU in a nutrient medium, wherein the cultures of at least two *Trichoderma* spp. comprise a culture of *Trichoderma reesei* MCC 0174 and a culture of one or more of *Trichoderma* spp. selected from *Trichoderma longibrachiatum* MCC 0169, *Trichoderma erinaceum* MCC 0168, *Trichoderma longibrachiatum* MCC 0171 and *Trichoderma hamatum* MCC 0170; wherein a ratio of *Trichoderma reesei* MCC 0174 to the one or more *Trichoderma* spp. in the consortium is in a range of 0.5:1 to 1:10 or 1:0.5 to 1:10.

2. The consortium as claimed in claim 1, wherein the consortium comprises a culture of:

*T. reesei* MCC 0174, *T. longibrachiatum* MCC 0169 and *T. erinaceum* MCC 0168 in a ratio of 0.5:1:0.5 to 1:5:0.5;

*T. reesei* MCC 0174, *T. longibrachiatum* MCC 0169 and *T. hamatum* MCC 0170 in a ratio of 0.5:1:0.5 to 1:5:0.5;

*T. reesei* MCC 0174, *T. longibrachiatum* MCC 0171 and *T. erinaceum* MCC 0168 in a ratio of 0.5:1:0.5 to 1:5:0.5; or

*T. reesei* MCC 0174, *T. longibrachiatum* MCC 0171 and *T. hamatum* MCC 0170 in a ratio of 0.5:1:0.5 to 1:5:0.5.

3. The consortium as claimed in claim 1, wherein the consortium comprises a cultures of:

*T. reesei* MCC 0174*, T. erinaceum* MCC 0168, *T. hamatum* MCC 0170 and *T. longibrachiatum* MCC 0169 in a ratio of 0.5:1:1:0.5 to 3:1:1:5; or

*T. reesei* MCC 0174*, T. erinaceum* MCC 0168, *T. hamatum* MCC 0170, *T. longibrachiatum* MCC 0171 in a ratio of 0.5:1:1:0.5 to 3:1:1:5.

4. The consortium as claimed in claim 1, wherein the consortium comprises a cultures of *T. reesei* MCC 0174*, T. erinaceum* MCC 0168, *T. hamatum* MCC 0170, *T. longibrachiatum* MCC 0169 and *T. longibrachiatum* MCC 0171 in a ratio of 0.5:0.5:0.5:1:1 to 3:1:1:5:5.

* * * * *